US005833647A

United States Patent [19]
Edwards

[11] Patent Number: 5,833,647
[45] Date of Patent: Nov. 10, 1998

[54] HYDROGELS OR LIPOGELS WITH ENHANCED MASS TRANSFER FOR TRANSDERMAL DRUG DELIVERY

[75] Inventor: David A. Edwards, State College, Pa.

[73] Assignee: The Penn State Research Foundation, University Park, Pa.

[21] Appl. No.: 541,538

[22] Filed: Oct. 10, 1995

[51] Int. Cl.[6] .................................................. A61B 17/20
[52] U.S. Cl. ........................ 604/22; 604/49; 604/890.1
[58] Field of Search ................................. 604/20–21, 49, 604/290; 601/2

[56] References Cited

U.S. PATENT DOCUMENTS

| | | |
|---|---|---|
| 4,657,543 | 4/1987 | Langer et al. . |
| 4,767,402 | 8/1988 | Kost et al. . |
| 4,779,806 | 10/1988 | Langer et al. . |
| 4,780,212 | 10/1988 | Kost et al. . |
| 4,948,587 | 8/1990 | Kost et al. . |
| 5,013,293 | 5/1991 | Sibalis . |
| 5,019,034 | 5/1991 | Weaver et al. . |
| 5,019,372 | 5/1991 | Folkman et al. . |
| 5,152,758 | 10/1992 | Kaetsu et al. . |
| 5,224,927 | 7/1993 | Tapper . |
| 5,302,172 | 4/1994 | Sage, Jr. et al. . |
| 5,312,325 | 5/1994 | Sibalis . |
| 5,328,454 | 7/1994 | Sibalis . |
| 5,336,168 | 8/1994 | Sibalis . |
| 5,372,579 | 12/1994 | Sibalis . |
| 5,415,629 | 5/1995 | Henley . |
| 5,462,520 | 10/1995 | Hofmann . |
| 5,582,586 | 12/1996 | Tachibana et al. . |

FOREIGN PATENT DOCUMENTS

| | | |
|---|---|---|
| 625360 | 11/1994 | European Pat. Off. . |
| 3170172 | 7/1991 | Japan . |
| 931191 | 5/1982 | U.S.S.R. . |
| 100853 | 3/1983 | U.S.S.R. . |

OTHER PUBLICATIONS

Brochure, "Lectro Patch®Drug Delivery", General Medical Company.
Mitragotri et al . . "Ultrasound–Mediated Transdermal Protein Delivery", *Science*, vol. 269, Aug. 11, 1995, pp. 850–853.
Mitragotri et al . . "A Mechanistic Study of Ultrasonically–Enhanced Transdermal Drug Delivery", *Journal of Pharmaceutical Sciences*, vol. 84, No. 6, Jun. 1995, pp. 697–706.
Prausnitz et al., "Electroporation of mammalian skin: A mechanism to enhance transdermal drug delivery", *Proc. Natl. Acad. Sci. USA*, vol. 90, Nov. 1993, pp. 10504–10508.

*Primary Examiner*—Mark Bockelman
*Attorney, Agent, or Firm*—Thomas J. Monahan

[57] ABSTRACT

The present invention comprises a method of transdermal drug delivery where a drug is contained in or must pass through a hydrogel or lipogel together with an enhancement method to improve mass transfer through the skin, the improvement comprising applying a means for enhancing mass transfer of the drug through the hydrogel or lipogel to the skin.

6 Claims, 4 Drawing Sheets

HYDROGELS OR LIPOGELS WITH ENHANCED MASS TRANSFER FOR TRANSDERMAL DRUG DELIVERY

BACKGROUND OF THE INVENTION

1. Field of the Invention

The invention relates to a method of enhancing mass transfer of drugs through hydrogels or lipogels for transdermal drug delivery.

2. Description of the Prior Art

Delivery of drugs to obtain therapeutically significant systemic blood levels of a drug has traditionally been administered by oral or parenteral routes. Such delivery routes have drawbacks. Drugs delivered orally frequently are degraded in the gastrointestinal tract or liver. The drug itself may also forestall or compromise drug absorption due to a patient's reaction to the drug in the gastrointestinal tract. Parenteral drug delivery is associated with pain from injection and risks of infection from needle sticks. Frequent administration of injected drugs is cumbersome for most patients. Moreover, sustained or controlled delivery of a drug by these conventional routes of administration is problematic. To overcome these drawbacks, recent efforts have been aimed at more efficient drug delivery systems, namely, transdermal drug delivery systems.

Transdermal delivery systems typically comprise a "patch" comprising an active agent dispersed in a carrier, such as a gel. Clinical use of transdermal drug delivery has been limited because very few drugs are able, at least by passive diffusion alone, to penetrate the skin at a sufficient rate to produce a useful systemic drug concentration in the patient. The outer layer of the skin, the stratum corneum, is a major barrier to diffusion of low and especially high molecular weight drugs across the skin to the bloodstream. The drugs which are particularly sought for transdermal delivery include therapeutic agents (e.g., insulin, vasopressin) and non-therapeutic markers (e.g., fluorescent calcein). These drugs constitute examples of molecules which do not readily diffuse through the stratum corneum at a therapeutically useful rate.

Skin permeabilization techniques have been used to alter the structure of the lipid bilayer of the stratum corneum in order to allow such drugs to pass through the skin. Techniques for skin permeabilization include sonophoresis and electroporation. Other techniques, such as iontophoresis, involve forced diffusion of a drug through the skin, but do not necessarily alter skin structure.

Sonophoresis (the transport of drugs through the skin in the presence of an acoustic wave) potentially changes the skin structure by creating transient "holes" (regions of low resistance to drug transport) in the skin. A low or high frequency ultrasound field is applied across the skin by placing a transducer above the surface of the skin. The transducer is typically immersed in a gel-like medium that bathes the area of the skin across which molecular transport occurs. Sonophoresis appears to cause cavitation within the stratum corneum and leads to a temporary break of the lipid bilayer structure thus increasing the permeability of the skin. This technique is described in U.S. Pat. No. 4,767,402.

Electroporation also changes the skin structure by creating transient aqueous pores in the lipid bilayers of the skin during the application of brief electric fields. Transdermal electric field voltages of 100 volts and higher are applied to the skin to create "holes" in the skin through which drugs may pass. Such a technique is described in U.S. Pat. No. 5,019,034.

A third method for inducing transfer of drugs across the skin is iontophoresis. It is not a skin permeabilization technique. Iontophoresis employs a low voltage electric field which does not change the skin structure but induces transfer of charged molecules via ionic drift. This technique is described in U.S. Pat. No. 5,224,927 and is commercially embodied, for example, in Lectro Patch® sold by General Medical Company of Los Angeles, Calif.

Each of these techniques and other techniques for enhancing mass transfer across the stratum corneum reduce or eliminate the diffusion barrier presented by the stratum corneum in transdermal drug delivery. In any of these skin permeabilization or transport enhancement techniques, the skin presents a barrier of about 15 microns in thickness through which a drug must diffuse. However, the drug typically is contained in a patch (or pad) which can potentially present an even greater diffusion barrier of about 1 mm in thickness. This potential barrier is especially problematic for skin permeabilization methods of transdermal drug delivery. Because drugs can diffuse very rapidly through the skin using these methods, it is possible that the diffusion barrier of the patch itself can reduce the overall rate of transdermal drug delivery. Because the concentration gradient is inversely proportional to the thickness of the barrier, the concentration gradient in the skin is normally much greater than that in a transdermal patch. A high concentration gradient results in a high rate of diffusion for skin permeabilization methods (since the barrier property of the skin is temporarily substantially reduced) while a low concentration gradient results in a low rate of diffusion. Therefore, since the concentration gradient of the skin now may be overcome by skin permeabilization techniques, the transfer of drugs through a transdermal patch can potentially be limited by the relatively low concentration gradient present in the patch.

Transdermal patches which may be used alone or in conjunction with skin permeabilization techniques typically are made of three-dimensional macromolecule networks, hydrogels or lipogels (or simply "gels"), whose interstices are filled either with an aqueous continuous phase (i.e., a hydrogel) or a nonaqueous continuous fluid phase (i.e., a lipogel). Examples include aqueous or nonaqueous fluid-filled polymer or polysaccharide networks composed of methyl cellulose, dextrans, polyvinyl alcohol, agarose, hyaluronic acid, polyacrylamide and other such polymers. It is believed that hydrogels or lipogels can prevent significant convective mixing leading to the development of an unstirred diffusion layer in the gel, the thickness of which is much greater than the thickness of the stratum corneum. Forced or molecular diffusion may itself be substantially reduced by absorption of the drug to the polymer network within the gel. In either case, the gel provides a barrier to transport of the drug to the skin, one that becomes especially substantial when the skin is temporarily permeabilized.

Even when patches are not used for transdermal drug delivery, hydrogels or lipogels normally are required for sonophoresis. Dermal application of ultrasound typically involves a hydrogel or lipogel as the coupling medium through which the acoustic field is transferred to the skin. The use of a gel not only permits transfer of the acoustic field to the skin but potentially minimizes the pain associated with low or high frequency sonophoresis surrounding the area of the transducer. Gels can also provide a medium for "higher loading" of the drug than is available in aqueous systems. Proteinaceous drugs can also be stabilized (kept in proper conformation) when enclosed within a gel. Low frequency sonophoresis for skin permeabilization in transdermal drug delivery is described in Mitragotri et al., "Ultrasound-Mediated Transdermal Protein Delivery", *Science*, Vol. 269, pp. 850–853 (1995) which reports transdermal delivery and control of therapeutic doses of high molecular weight drugs including insulin, interferon-γ and erythropoeitin. Mitragotri et al. express the current prevailing opinion that the stratum corneum (and not the transdermal patch or external coupling medium) is the chief barrier to transdermal molecular transport, but also recognize that the ultrasound coupling medium is a yet nonoptimized parameter in sonophoresis for transdermal drug delivery.

Thus, the use of a hydrogel or lipogel in transdermal drug delivery (either as a sonophoresis coupling medium or in a patch) is common and potentially beneficial yet currently problematic when associated with skin permeabilization methods. Therefore, a need remains for a method to enhance mass transfer of drugs through a hydrogel or lipogel, thereby permitting the efficacious use of gels with skin permeabilization methods, such as sonophoresis and electroporation.

SUMMARY OF THE INVENTION

In order to meet this need, the present invention is a method for improving mass transfer of a drug through a hydrogel or lipogel to the skin of a patient. Skin permeabilization techniques typically are used to improve mass transfer through the skin, but the hydrogel or lipogel itself can remain as a significant barrier to diffusion of the drug to the skin. The present invention comprises the use of any mass transfer driving force other than the concentration gradient of the drug to enhance mass transfer of the drug through a hydrogel or lipogel simultaneously with skin permeabilization methods. The mass transfer driving force may be an applied external field that acts on solvent or drug molecules leading to convection or forced oscillation of gel fibers resulting in improved mixing within the gel. Convection includes mass transfer induced by a pressure gradient or forced diffusion produced by an electric field or acoustic field. An electric field is produced by applying a direct current of about 0.001 mA to 10 mA across the thickness of the hydrogel or lipogel. The electric field may be controlled in a manner such that diffusion of the drug through the gel to the simultaneously permeabilized skin can be controlled and thus true controlled transdermal drug delivery is achieved. Temperature gradients and oscillating magnetic fields can also be used to accomplish enhanced mass transfer.

DETAILED DESCRIPTION OF THE INVENTION

Figure 1:
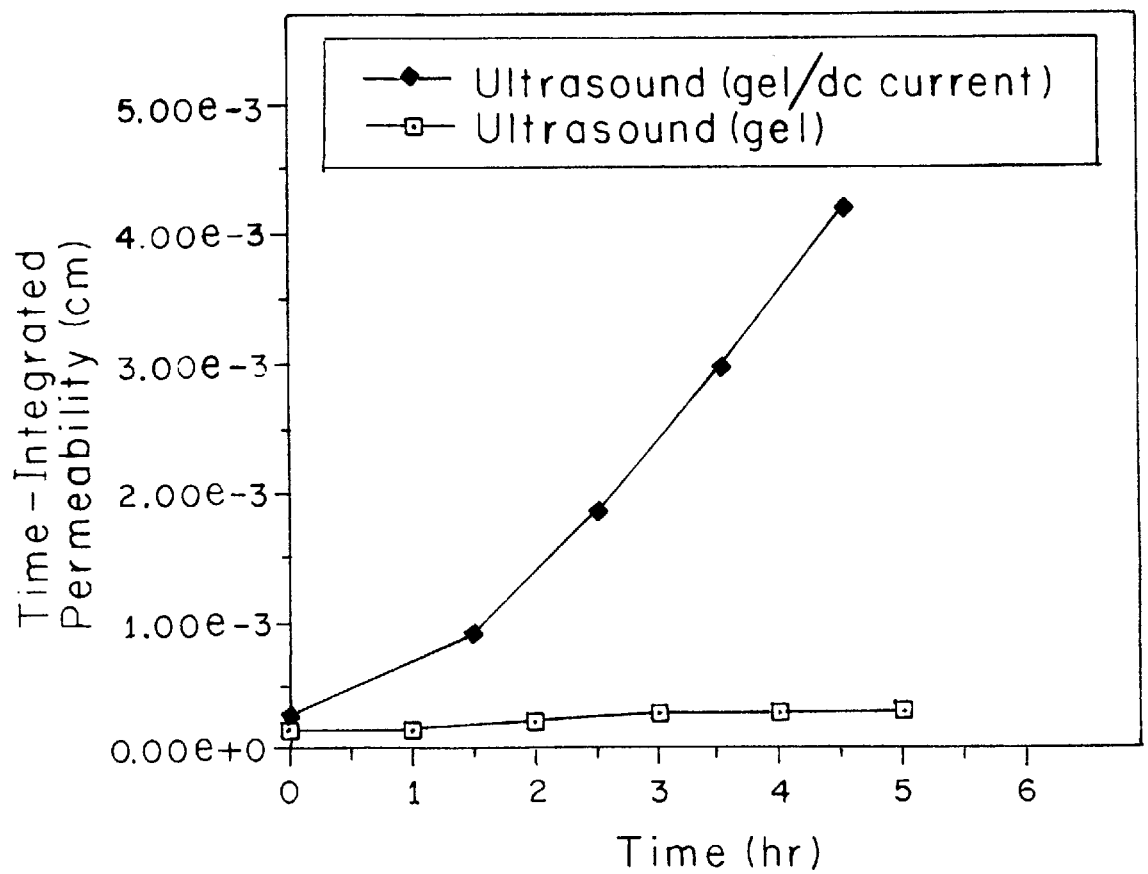
FIG. 1 is a graph of the time-integrated skin permeability of vasopressin transported across skin via ultrasound through gel, with and without direct current.
Figure 2:
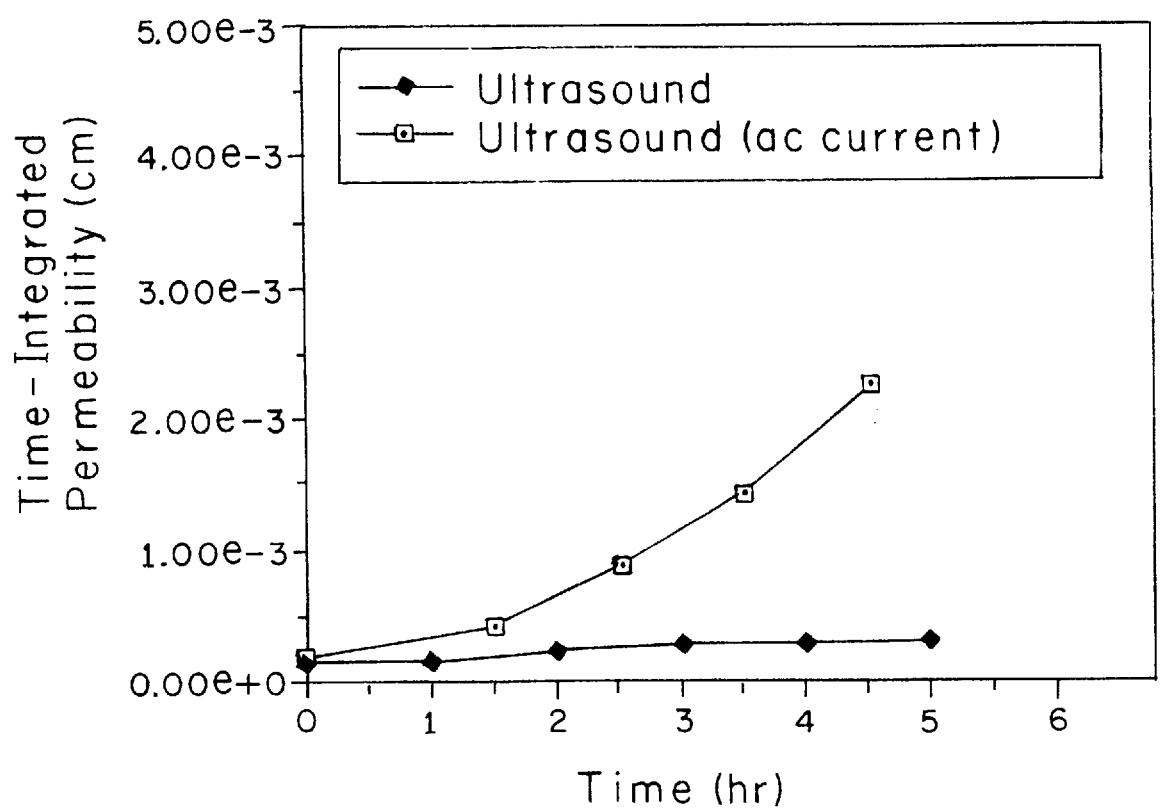
FIG. 2 is a graph of the time-integrated skin permeability of vasopressin transported across skin via ultrasound through gel, with and without alternating current.

The mass transfer enhancement methods of the present invention are suitable for simultaneous use with skin permeabilization techniques or other methods of enhancing mass transfer through the skin (i.e., those that result in a major, temporary loss of the normal transport barrier function of the skin). The present invention comprises a method for enhancing mass transfer of a drug through a hydrogel or a lipogel used in conventional transdermal drug delivery systems. Transdermal drug delivery systems may employ a skin permeabilization technique which reduces or removes the barrier to diffusion of the drug through skin posed by the stratum corneum. The hydrogel or lipogel present in transdermal patches or used as a coupling medium in ultrasonic mediated transdermal delivery potentially poses an additional diffusion barrier.

The invention comprises a method of inducing convection of a drug through a hydrogel or lipogel, in particular, wherein the driving force for transport of the drug through the gel is produced by an external or internal driving force other than the concentration gradient of the drug. The resultant enhanced mass transfer may be termed convection as distinguished from the molecular diffusion induced by the drug concentration gradient inherent in the hydrogel or lipogel. A field is applied to the hydrogel or lipogel containing a drug to enhance the mass transfer of the drug through the hydrogel or lipogel. The field applied to the hydrogel or lipogel reduces or removes the barrier posed by the gel to transdermal molecular transport by enhancing mass transfer in the gel relative to the mass transfer which accompanies the transdermal molecular transport in the absence of the applied field. Convection may be induced by the application of a pressure gradient or a forced diffusion field. Examples of a forced diffusion field include an electric field (a voltage gradient), a temperature gradient, and an acoustic field. Alternatively, mass transfer of the drug may be enhanced by improving mixing within the gel. Mixing can be improved, for example, by producing agitation of the gel network.

In particular, the skin permeabilization method of low frequency (20 kHz) sonophoresis typically includes use of a hydrogel or lipogel which poses a major barrier to transdermal molecular transport due to an unstirred layer in the hydrogel or absorption of the drug molecules within the hydrogel or lipogel. The present invention dramatically reduces or removes this transport barrier.

According to one embodiment of the invention, iontophoresis is used to enhance mass transfer of a drug through a hydrogel or lipogel. A direct current is applied across a hydrogel or lipogel in which is dispersed a drug for transdermal delivery. The hydrogel or lipogel is applied to the skin and may be in the form of an ultrasound coupling medium or an integral part of a self-contained transdermal patch. Application of direct current across the hydrogel or lipogel causes the drug molecules to be pushed through the hydrogel or lipogel in the direction of the resulting electric field (voltage gradient). A current of about 0.001 mA to 10 mA, preferably 0.1 mA, is applied to the hydrogel or lipogel. The precise amperage is selected to induce ionic drift of the drug at a sufficient rate to deliver the drug to the skin for ultimate transport across the skin to achieve controlled drug delivery. Because the skin is a reduced barrier to molecular transport when skin permeabilization techniques are used, by controlling the rate of ionic drift of the drug through the hydrogel or lipogel, true controlled transdermal drug delivery is achieved.

In another embodiment of the invention, alternating current of about 0.001 mA to 10 mA at about 0.1 Hz to megahertz frequencies, preferably 0.1 mA at 1 Hz, is applied to the drug-containing hydrogel or lipogel. The alternating current essentially rocks the drug and possibly the molecules of the hydrogel or lipogel back and forth to induce mixing within the hydrogel or lipogel, thereby eliminating or reducing the unstirred layer in the gel. The alternating current electric field may also induce electroosmotic motion of solvent molecules back and forth within the gel effectively stirring the contents of the gel. Such electroosmotic motion results from the alternating current electric field rocking ions gathered near charged fibers of the gel, whereby the ions drag solvent molecules in the direction of their motion. This phenomenon may occur even though the drug itself is not charged.

The invention also includes other methods of mass transfer enhancement which can reduce and/or remove the transport barrier of an unstirred layer in a hydrogel or lipogel and/or cause the release of molecules absorbed within the hydrogel or lipogel. A temperature gradient may be used to enhance mass transfer. A heat source is applied to the hydrogel or lipogel which produces a temperature gradient and effects a phase change in the hydrogel or lipogel. The phase change induces volume expansion and/or contraction within the gel and thus disrupts the unstirred layer through the gel.

An oscillating magnetic field combined with magnetic dipoles dispersed through the gel may also be used to disrupt the unstirred layer through the gel. Magnetic dipoles are mixed into the drug-containing gel. When an oscillating magnetic field is applied to the gel, the dipoles agitate and thus cause mixing within the gel. This induced mixing enhances the mass transfer of the drug through the gel.

Other mechanisms which may be used to induce convection of a drug through a hydrogel or lipogel include a pressure gradient which forces the molecules to move through the gel and disrupts the unstirred layer in the gel.

The invention is applicable not only to drugs alone but also to carriers of drugs such as micelles, microemulsion droplets, liposomes, nanoparticles or microparticles (polymeric particles) and the like. These carriers may also be dispersed in a hydrogel or lipogel which presents a significant barrier to diffusion of such carriers to the skin. Thus, the present invention provides a method for improving mass transfer of drug carriers through a gel to the skin of a patient.

Although the invention has been described generally above, particular examples give additional illustration of the method steps typical of the present mass transfer enhancement method.

EXAMPLE 1

In Vitro Human Skin Tests (Vasopressin with direct current)

In each of the following tests, tritium labeled vasopressin (1084 Da, isoelectric point 10.9) was placed in a pH=4 buffer within the donor compartment of a Franz diffusion cell and was allowed to transport across human cadaver skin (female abdominal region). The time-integrated permeability of vasopressin across the cadaver skin for these experiments is shown in FIG. 1 as a function of time. Concentrations were measured by scintillation counting. In the first test, a pH=4 buffer containing vasopressin was equilibrated with a 2% methyl cellulose hydrogel (composed of 80K Da methyl cellulose in water). The hydrogel containing vasopressin was placed in the donor compartment of the diffusion cell and ultrasound (20 kHz, 10% duty cycle) was applied. An amount below the detection limit of vasopressin (skin permeability <$10^{-4}$ cm/h) was transported across the skin for the duration (5 hours) of the experiment. That is, the ultrasound-assisted transport rate of vasopressin across the cadaver skin was dramatically low in the presence of the hydrogel.

Figure 3:
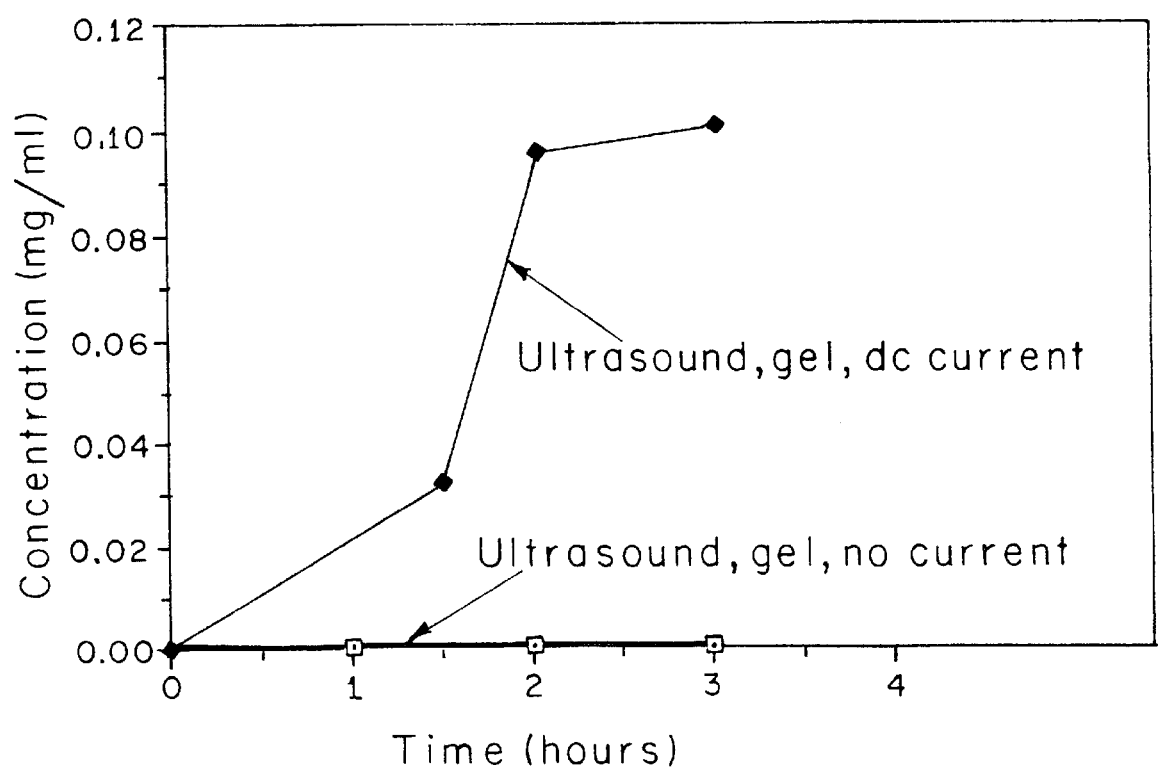
FIG. 3 is a graph of the concentration of calcein in the receiver compartment of a Franz cell over time transported through gel with and without direct current.

In the second test, an 0.1 mA direct current was applied simultaneously with ultrasound as in the first test to transport vasopressin from the hydrogel across the cadaver skin. The time-integrated permeability of vasopressin transported across the skin for this experiment is also shown in FIG. 1. A much greater transport rate of vasopressin was achieved from the gel by applying the ultrasound with a direct electric current (skin permeability approximately $10^{-2}$ to $10^{-3}$ cm/h) than by applying the ultrasound alone (skin permeability less than $10^{-4}$ cm/h). This owes to the fact that the direct current provides a non-concentration gradient driving force for the positively charged vasopressin transport through the hydrogel and skin, of sufficient magnitude to dominate the concentration gradient driving force of mass transfer which is rate limited by a diffusion boundary (or unstirred) layer in the hydrogel. That is, while the skin is permeabilized by the ultrasound, a heightened skin permeability does not permit the characteristically high transdermal transport rate associated with low-frequency ultrasound unless a method (in this case a direct current) is used to enhance the mass transfer through the gel.

EXAMPLE 2

In Vitro Human Skin Tests (Vasopressin with alternating current)

An alternating current (rather than direct) was used to enhance mass transfer in the hydrogel. Tritium labeled vasopressin (1084 Da, isoelectric point 10.9) was placed in a pH=4 buffer and equilibrated with a 2% methyl cellulose hydrogel. The vasopressin-containing gel solution was placed within the donor compartment of a Franz diffusion cell and transported across human cadaver skin (female abdominal region) in the presence of low-frequency ultrasound (20 kHz, 10% duty cycle) and an alternating current (approximately 0.1 mA, frequency 1 Hz). The difference between the alternating current used in this example and the direct current used in Example 1 is that little or no net iontophoretic transport is expected to accompany an alternating current. The alternating current causes the charged vasopressin to move back and forth within the gel and the skin, causing enhanced mixing while not causing a net, time-averaged forced diffusion of the vasopressin through the gel and skin.

The relative amount of vasopressin transported across the cadaver skin in the presence of the ultrasound and the alternating current is shown in FIG. 2 as a function of time. Also shown is the ultrasound-assisted transport rate from the pH=4 buffer when an alternating current is not applied. The effect of the alternating current is to lead to a significantly greater transport enhancement from the hydrogel in the presence of the ultrasound. This demonstrates that achieving a high rate of transdermal transport from a hydrogel in the presence of a skin permeabilization method, such as sonophoresis, can be achieved by enhancing mixing in the hydrogel, as occurs with application of an alternating current.

EXAMPLE 3

In Vitro Human Skin Tests (Calcein with direct current)

The transdermal transport of a second molecule, calcein (623 Da, charge=−4), across human cadaver skin (female abdominal region) was studied in an in vitro Franz diffusion cell apparatus. Like vasopressin, calcein is unable to undergo a detectable transport across human skin in the absence of an applied external field owing to the natural barrier of the stratum corneum and the charge and size of the molecule. Using the same conditions as in Example 1, ultrasound (frequency 20 kHz, duty cycle 10%) was applied to the cadaver skin to cause skin permeabilization. Calcein, contained within a 3% methyl cellulose gel, was placed in the donor compartment of the Franz cell. The concentration of calcein in the receiver as a function of time is shown in FIG. 3 for two cases. In the first case, no direct current was applied, and in the second case, a direct current of approximately 0.1 mA was applied across the skin. It can be seen that, with the addition of a small electrical current, a relatively large transdermal transport of calcein can be achieved.

EXAMPLE 4

In Vitro Human Skin Tests (Insulin with alternating current)

Figure 4:
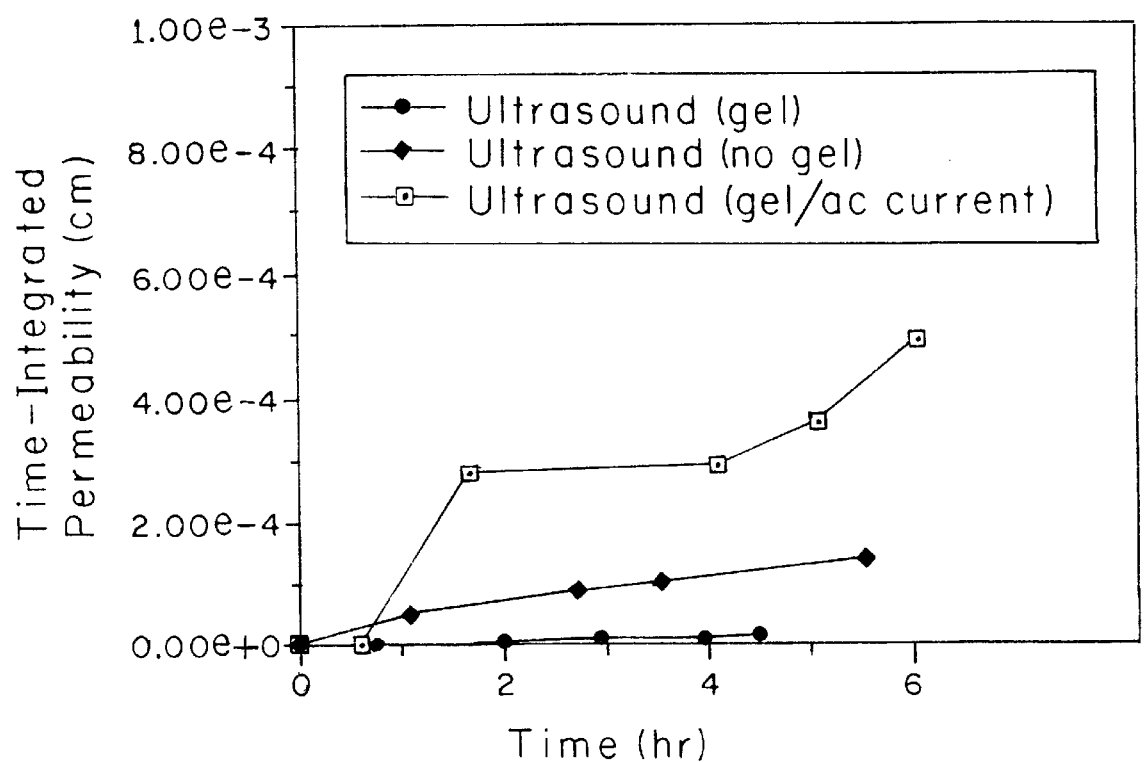
FIG. 4 is a graph comparing the time-integrated skin permeability of insulin transported via ultrasound through gel, via ultrasound in the absence of gel and via ultrasound and alternating current through gel.

The transport of $^{125}$I-labeled human insulin (~6000 Da, isoelectric point ~5.3) across human cadaver skin (female abdominal region) in an in vitro Franz diffusion cell apparatus was studied. Insulin is unable to undergo a detectable transport across human skin in the absence of an applied external field owing to the natural barrier of the stratum corneum and the large size of the molecule. Ultrasound (frequency 20 kHz, duty cycle 10%) has been used previously to cause skin permeabilization. When insulin is placed in the donor compartment of the Franz cell (no gel present, buffer of pH 7.4), the permeability of insulin after several hours of application is shown in FIG. 4. This skin permeability value is consistent with the literature value (Mitragotri et al.). As shown in FIG. 4, when the insulin is equilibrated with a 2% methyl cellulose hydrogel, the transdermal transport rate is undetectable (permeability $\leq 10^{-4}$ cm/h) after several hours of ultrasound application.

When an alternating current of approximately 0.1 mA (cathode in the donor compartment) was applied across the cadaver skin, enhanced mass transfer of the insulin was achieved. The transdermal permeability after several hours of application, with insulin placed within the 2% methyl cellulose hydrogel and ultrasound applied, is shown in FIG. 4. The resulting insulin permeability using ultrasound for skin permeabilization and alternating current to enhance mass transfer through the gel is about three times the permeability achieved with ultrasound alone. The applied alternating current electric field provides sufficient mixing to eliminate the concentration gradient of insulin across the hydrogel as well as to somewhat magnify the sonophoretic transport relative to that which is achieved without the gel and the alternating current electric field.

Although the invention has been described with particularity in the above text and examples, the invention is only to be limited insofar as set forth in the accompanying claims.

I claim:

1. In a method of transdermal drug delivery where a drug is contained in or must pass through a hydrogel or lipogel, said hydrogel or lipogel posing a barrier to drug delivery, together with a method of permeabilizing skin comprising applying low frequency ultrasound to the skin, the improvement comprising:

applying a means for mixing the drug within the hydrogel or lipogel; and enhancing the rate of drug delivery across the skin by said means for mixing the drug within the hydrogel or lipogel wherein said mixing comprises the steps of (a) mixing magnetic dipoles into said hydrogel or lipogel and (b) applying and oscillating magnetic field to said hydrogel or lipogel wherein said magnetic dipoles are agitated such that the molecules within said gel are agitated.

2. In a method of transdermal drug delivery where a drug is contained in or must pass through a hydrogel or lipogel, said hydrogel or lipogel posing a barrier to drug delivery, together with a method of permeabilizing skin comprising applying low frequency ultrasound to the skin, the improvement comprising:

applying a means for mixing the drug within the hydrogel or lipogel; and enhancing the rate of drug delivery across the skin by said means for mixing the drug within the hydrogel or lipogel wherein said mixing comprises applying a heat source to said hydrogel or lipogel to induce a phase change in said hydrogel or lipogel whereby said hydrogel or lipogel expands and/or contracts.

3. The method of claim 1 or 2 wherein said drug is selected from the group consisting of calcein, vasopressin and insulin.

4. The method of claim 1 or 2 wherein said drug is vasopressin.

5. The method of claim 1 or 2 wherein said drug is insulin.

6. The method of claim 1 or 2 wherein said drug is contained in carriers selected from the group consisting of micelles, microemulsion droplets, liposomes, nanoparticles and microparticles.

\* \* \* \* \*